United States Patent
Baco

(10) Patent No.: US 9,855,205 B2
(45) Date of Patent: Jan. 2, 2018

(54) USE OF ZINC COCETH SULFATE AS AN ANTIBACTERIAL AGENT AGAINST PROPIONIBACTERIUM ACNES

(71) Applicant: PIERRE FABRE DERMO-COSMETIQUE, Boulogne-Billancourt (FR)

(72) Inventor: David Baco, Labarthe sur Leze (FR)

(73) Assignee: PIERRE FABRE DERMO-COSMETIQUE, Boulogne-Billancourt (FR)

(*) Notice: Subject to any disclaimer, the term of this patent is extended or adjusted under 35 U.S.C. 154(b) by 0 days.

(21) Appl. No.: 14/413,646

(22) PCT Filed: Jul. 8, 2013

(86) PCT No.: PCT/EP2013/064391
§ 371 (c)(1),
(2) Date: Jan. 8, 2015

(87) PCT Pub. No.: WO2014/009315
PCT Pub. Date: Jan. 16, 2014

(65) Prior Publication Data
US 2015/0196474 A1 Jul. 16, 2015

(30) Foreign Application Priority Data
Jul. 9, 2012 (FR) .................... 12 56606

(51) Int. Cl.
*A61K 8/27* (2006.01)
*A61K 8/00* (2006.01)
*A61K 8/58* (2006.01)
*A61K 8/46* (2006.01)
*A61Q 17/00* (2006.01)
*A61Q 19/00* (2006.01)

(52) U.S. Cl.
CPC ............... *A61K 8/58* (2013.01); *A61K 8/27* (2013.01); *A61K 8/463* (2013.01); *A61Q 17/005* (2013.01); *A61Q 19/00* (2013.01); *A61K 2800/58* (2013.01)

(58) Field of Classification Search
CPC .......... A61K 8/463; A61K 8/466; A61K 8/58; A61K 8/27
See application file for complete search history.

(56) References Cited

U.S. PATENT DOCUMENTS 6,284,234 B1 * 9/2001 Niemiec ................ A61K 8/19
424/70.13
2002/0022660 A1 * 2/2002 Jampani ............... A61K 36/899
514/635

(Continued)

FOREIGN PATENT DOCUMENTS

EP 0 068 055 A1 1/1983
EP 1 074 247 A2 2/2001

(Continued)

OTHER PUBLICATIONS

Anonymous, "Zetesol ZN, An Alkyl Ether Sulfate with Surprising Applications," Zschimmer & Schwarz Italiana S.p.A., Mar. 2003, pp. 1-28, XP-002691939.

(Continued)

*Primary Examiner* — Lakshmi S Channavajjala
(74) *Attorney, Agent, or Firm* — Birch, Stewart, Kolasch & Birch, LLP

(57) ABSTRACT

The invention relates to zinc coceth sulfate for the use thereof as an antibacterial agent for treating skin disorders associated with *Propionibacterium acnes*.

4 Claims, 1 Drawing Sheet

(56) References Cited

U.S. PATENT DOCUMENTS

| | | | |
|---|---|---|---|
| 2006/0057090 A1 | 3/2006 | Buchwald-Werner | |
| 2010/0028458 A1* | 2/2010 | Bobbert | A61K 8/06 424/616 |
| 2012/0258065 A1 | 10/2012 | Dechelette et al. | |
| 2014/0121176 A1* | 5/2014 | Nadau Fourcade | A61K 8/365 514/33 |

FOREIGN PATENT DOCUMENTS

| | | |
|---|---|---|
| EP | 1 112 079 A1 | 7/2001 |
| EP | 2 399 576 A1 | 12/2011 |
| WO | WO 00/16791 A | 3/2000 |
| WO | WO 2011/073370 A2 | 6/2011 |
| WO | WO 2012/163928 A2 | 12/2012 |

OTHER PUBLICATIONS

Bigotti et al., "Zinc and Its Derivatives: Their Applications in Cosmetic," J. App. Cosmetol, vol. 23, Oct./Dec. 2005, pp. 139-147.

International Search Report, dated Sep. 11, 2014, for International Application No. PCT/EP2013/064391.

Personal Care Products Council, "Sodium Lauroyl Methyl Isethionate," International Cosmetic Ingredient Dictionary and Handbook, Jan. 1, 2010, pp. 2863.

English Machine Translation of EP 0 068 055, Jan. 1, 1983.

English Machine Translation of WO 00/16791, Mar. 30, 1990.

\* cited by examiner

USE OF ZINC COCETH SULFATE AS AN ANTIBACTERIAL AGENT AGAINST PROPIONIBACTERIUM ACNES

The field of this invention relates to the new antibacterial properties of zinc coceth sulfate against the bacterium *Propionibacterium acnes*; and its applications in the fields of cosmetics and of dermatology for the treatment of acne and skin disorders associated with *Propionibacterium acnes*.

Sebum is the secretion by the sebaceous glands of the skin of a lipidic film which is used to protect it and, mixed with sweat, protects the skin from drying out.

Sebum allows for the waterproofing of the skin, participates in the development of the epidermal structure. It protects it from microbes by acidifying it (presence of lactic acid and of fatty acids) and assures a certain degree of impermeability. It allows the skin to be supple and participates in the development of the epidermis.

Sebum normally arrives on the surface of the skin by the pores of the hair follicles.

During acne, the excess sebum in the hair follicle infundibulum represents an environment that is favourable for the colonisation of *Propionibacterium acnes*. The appearance of lesions in the acne depends on an excessively intense pro-inflammatory response, via innate immunity receptors, with regards to an excessively high density in *Propionibacterium acnes*.

These bacteria have in fact the particularity of metabolising the triglycerides of the sebum by releasing fatty acids which cause the inflammation of tissue.

Figure 1:
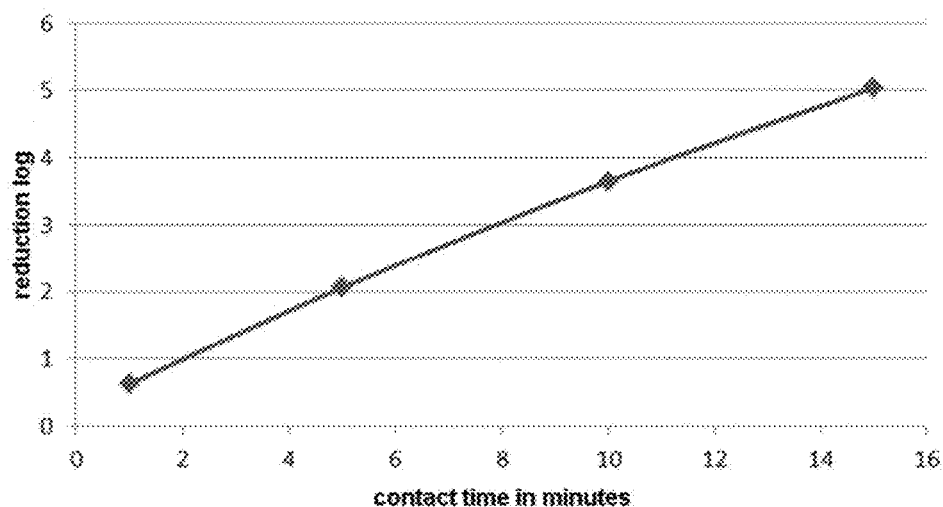
FIG. 1 is a graph showing the logarithmic reduction of the number of germs in relation to the initial number of germs over a contact time in minutes.

Unexpectedly and surprisingly, the applicant identified that zinc coceth sulfate can be used as an antibacterial agent against *Propionibacterium acnes*.

Zinc coceth sulfate (Zetesol Zn® from the company Zchimmer & Schwarz) is an anionic surfactant of which the tolerance is much higher than lauryl ether sulfate of conventional sodium due to the second lauryl chain fixed on the metal. The molecular presence of the zinc confers upon it an activity that is very interesting on the germs of oily skin and makes it possible to substantially limit the preservatives (concentration between 2% and 7%).

Zinc coceth sulfate is new generation surfactant, combining an alkyl ether sulfate with zinc (lipophilic double chain of Copra/zinc).

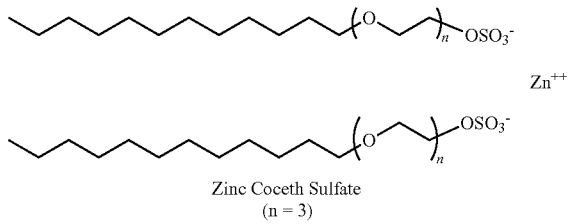

Zinc Coceth Sulfate
(n = 3)

Alkyl ether sulfates are the most widely used surfactants in cosmetic and toiletry products. Combined with binary or ternary mixtures, they are appreciable foaming agents (not affected by hard water) and have an excellent cleansing power.

They offer good skin and ocular tolerance which can be further improved according to the cation used to neutralise them.

The study carried out on zinc coceth sulfate made it possible to demonstrate not only that it developed good surfactant properties combined with an excellent local tolerance, but also that it was provided with other interesting properties.

Like alkyl ether sulfates, zinc coceth sulfate confirmed its good cleansing properties: satisfactory foaming power, obtaining of a soft and creamy foam, pleasant to use.

Its compatibility with the skin appeared however astonishing, as its potential for skin aggression is much less than that of alkyl ether sulfates and most likely linked to its lipophilic double chain.

Its cleansing power was furthermore shown to be indifferent to the hardness of the water.

Zinc coceth sulfate has an acidic pH of 4.5, close to the skin pH of about 5.5.

It therefore is not harsh to the skin of which the acidity is one of the major characteristics in adults as well as in young children.

Zinc coceth sulfate was shown to be devoid of any irritant and sensitising potential.

Zinc coceth sulfate has also proven it good tolerance on the mucosa.

This was demonstrated was made using the Het Cam test of which the principle is based on observing the irritant effects of a product that can occur within five minutes after it is deposited onto the chorio-allantoic membrane of an embryonated chicken egg, on the tenth day of incubation. Zinc coceth was tested in a 1% solution.

The bacteriological study was carried out on aqueous solutions of zinc coceth sulfate at 10% and 20% with a final pH between 5 and 6.

The bacteriological study was carried out on *Propionibacterium acnes*, bacterium responsible for acne-prone skin: a study conducted in the microbiology laboratory demonstrated this bactericidal efficacy. This study was confirmed on the finished product.

This invention therefore relates to a skin hygiene composition comprising zinc coceth sulfate as an antibacterial agent against *Propionibacterium acnes* combined with sodium lauryl methyl isethionate. According to another characteristic of the invention, said composition is useful as an antibacterial agent against *Propionibacterium acnes*. More particularly, said composition is intended for the treatment of acne.

Another aspect of this invention relates to the non-therapeutic use of a composition comprising zinc coceth sulfate as an antibacterial agent against *Propionibacterium acnes*.

Contrary to certain skin cleansing compositions of a similar type that qui advocate the required presence of salt or additional derivative of glycyrrhizic acid or glycyrrhetinic acid, the composition that is the object of this application is expressly devoid of such salts or additional derivatives.

Preferably, the cosmetic use is intended for the treatment and/or the hygiene of acne-prone skin and/or oily skin with acneic tendency.

The hygiene of acne-prone skin and/or oily skin with acneic tendency requires the use of products adapted to the tissue fragility and to the microbial flora that accompany the pathology.

Preferably, within the framework of the development of a cleansing product for acne-prone skin and/or oily skin with acneic tendency, it is necessary to satisfy several criteria:

- Good lipid-removing power of the sebacic fatty substances
- Good surfactant tolerance in such a way as to not stimulate the sebaceous gland through the rebound effect
- Regulate the sebaceous function
- Block the associated bacterial growth.

Another object of this invention relates to a composition, more preferably a cleansing composition for acne-prone skin and/or with acneic tendency comprising zinc coceth sulfate as an antibacterial agent against *Propionibacterium acnes* in association with

- the anionic surfactant sodium lauryl methyl isethionate;
- and/or another antibacterial agent chosen from among extract of myrtle and more particularly the extract of myrtle such as described in EP1112079, polyglyceryl-3 monocaprylate, glyceryl caprate, cetrimonium bromide,
- and/or an anti-seborrhoea agent chosen from among glyceryl laurate such as described in WO2011/073370, sabal extract, pumpkin seed oil, extract of *urtica* dioic, etc.

In a particular embodiment of the invention, the excipiendary base of the composition according to the invention combines anionic surfactants as a substantially binary mixture, of which zinc coceth sulfate possibly combined with sodium lauryl methyl isethionate; and non-ionic surfactants in a ratio of 80/20 expressed in active ingredient. The presence of an amphoteric substance at a low concentration furthermore makes it possible to stabilise the final viscosity.

Sodium lauryl methyl isethionate (Iselux®, Innospec) is, in the class of anionic surfactants, one of the better tolerated. Its use in dermobar for many years, confirms its excellent biocompatibility with skin, in the field of paediatrics as well as that of atopy (concentration between 5% and 10%).

In another preferred embodiment of the invention, zinc coceth sulfate as an antibacterial agent against *P. acnes* will be used combined with another active ingredient:

- antibacterial such as extract of myrtle and preferentially the extract of myrtle described in EP1112079, polyglyceryl-3 monocaprylate, glyceryl caprate, cetrimonium bromide
- or complementary action on the acne pathology such as glyceryl laurate, sabal extract, pumpkin seed oil, extract of *urtica* dioic.

Preferentially, the anionic surfactants zinc coceth sulfate and sodium lauryl methyl isethionate such as Iselux® will be combined in a skin cleansing and disinfecting composition.

Furthermore, it is known that bipolar non-ionic surfactants provide the product with extreme gentleness due to their molecular structure that combines their fatty chain with an oxyethylenated chain in the form of ether:

- polysorbate 20 combining cyclised sorbitol with an ethoxylated laurel chain
- ethoxylated hydrogenated castor oil (40EO)
- ceteareth-60 myristyl glycol of which the fatty chain provides skin surface protection.

Buffered at pH=5 by EDTA 2Na and citric acid, the formula is perfectly suited to the skin pH of oily skin. The acidic pH participates in the antibacterial and anti-5-alpha-reductase activity of the glyceryl laurate combined with the anti-inflammatory zinc gluconate.

Preferentially, the compositions according to the invention will be administered topically.

More preferentially, the compositions according to the invention have the form of a liquid cleansing gel, a foamer or an aerosol.

It is finally another object of this invention to provide a cosmetic method of purifying (and/or of cleansing) acne-prone skin and/or oily skin with acneic tendency characterised in that a composition comprising zinc coceth sulfate is applied on said skin.

The invention can be better understood using the following non-restricted examples and which constitute particular embodiments of the cosmetic and/or dermatological compositions according to the invention.

EXAMPLES OF COMPOSITION ACCORDING TO THE INVENTION

Example 1

Sodium Lauryl methyl isethionate (Iselux®, Innospec) from 5 to 20% Zinc coceth sulfate (Zetesol Zn®, Zchimmer & Schwarz) from 5 to 20% Disodium coco-amphoacetate from 3 to 10%

Polysorbate 20 from 0.5 to 4%

Ceteareth-60 myristyl glycol from 0.5 to 1.5%

Ethoxylated hydrogenated castor oil from 0.5% to 2%

Glyceryl laurate from 0.1 to 1%

Zinc gluconate from 0.1 to 0.5%

Citric acid/EDTA 2Na qsp pH=5

Evaluation of the Bactericidal Activity of Zetesol Zn® Against *P. acnes*.

The reduction over time of the log 10 of the number of germs in relation to initial number of germs (log R parameter) is evaluated.

The strain tested is *Propionibacterium acnes* ATCC6919.

Zetesol Zn® was tested at the concentration of 20% (i.e. 5% of active ingredient zinc coceth sulfate).

Method placing into contact of the product to be tested with suspensions of *P. acnes* titrated at about $10^6$ CFU/ml for 1, 5, 10 and 15 minutes.

Viable count after each duration of contact by inclusion of 1 ml of the sample in a culture agar (Columbia)

Incubation 72 hours at 36° C. in anaerobic conditions

Viable count of residual bacteria via direct counting.

Calculation of the fall in log 10:

The count of the dishes is carried out and this result is compared to a number of CFU/ml.

The calculation of the fall in log 10 of the number of CFU/ml is carried out according to the formula hereinbelow:

Logarithmic reduction=LOG 10(number of CFU present at T0/number of CFU remaining at Tx)

The results indicated in table 1 are the average of two independent tests (except for the duration of 10 min where only 1 test was carried out). Also see FIG. 1.

TABLE 1

| Concentration of Zetesol ® Zn | Log Reduction in 1 minute | Log Reduction in 5 minutes | Log Reduction in 10 minutes | Log Reduction in 15 minutes |
|---|---|---|---|---|
| 20% | 0.63 | 2.06 | 3.65 | >5.04 |

Good bactericidal activity is observed right from the first minute of contact which is close to the time of use for a rinsed product.

The activity is optimal at 15 minutes (maximum viewable threshold reached).

Example 2

Another example of composition according to the invention was subjected to the same evaluation of the bactericidal activity in accordance with the same protocol mentioned hereinabove.

Said composition tested satisfies the following formulation:
- Zetesol Zn (concentration 20%, i.e. 5% of active ingredient zinc coceth sulfate)
- Iselux (concentration 10%, i.e. 8% of active ingredient sodium lauroyl methyl isethionate)
- Ceteareth-60 myristyl glycol-thickening agent
- Cocoamphoacetate Na—amphoteric surfactant
- Capryl glycol
- Lactic acid
- NaOH
- Qs water The results obtained are shown in Table 2 herein below:

TABLE 2

|  | Log Reduction in 1 minute | Log Reduction in 5 minutes | Log Reduction in 10 minutes | Log Reduction in 15 minutes |
|---|---|---|---|---|
| Zetesol Zn 20% + Iselyx 10% | 1.9 | 2.6 | 3.5 | >4.2 |

A reduction of 1.9 log is observed in 1 minute on the strains of *Propionibacterium acnes* ATCC6919. It appears as such that the adding of sodium lauryl methyl isethionate made it possible to significantly improve the bactericidal activity of zinc coceth sulfate against *P. acnes*.

Evaluation of the Bactericidal Activity of the product Formulated According to the Example 1 against *P. acnes*.

The same protocol as hereinabove is used.
Product Tested:
 composition according to the example 1 diluted to 20% in sterile distilled water=use dilution of a rinsed product.
The strains tested are
*Propionibacterium acnes* ATCC6919.
*Propionibacterium acnes* Sauvage (R erythromycin-resistant strain)
*Propionibacterium acnes* Sauvage (S erythromycin-sensitive strain)

Figure 2:
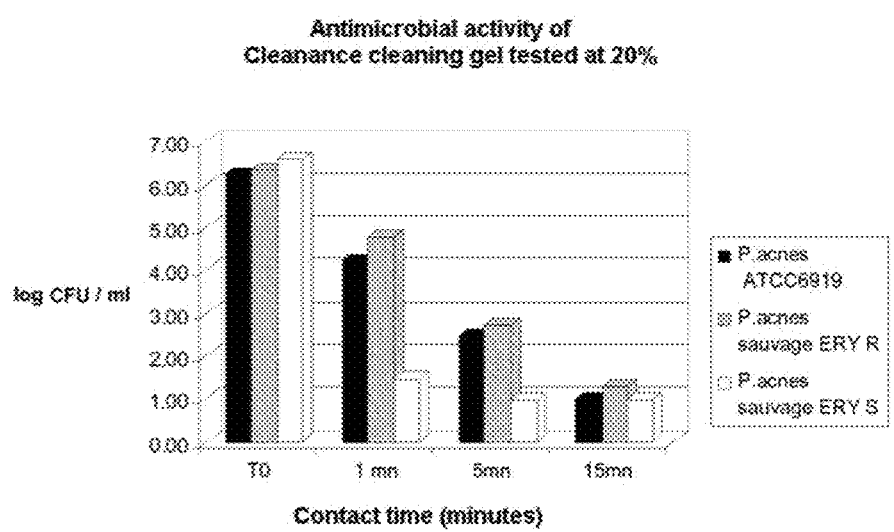
FIG. 2 is a graph showing the antimicrobial activity of the product formulated according to Example 1 against *P. acnes*.

The results indicated in table 3 hereinbelow are the average of 2 independent tests. Also see FIG. 2.

TABLE 3

| Germs | Log Reduction in 1 minute | Log Reduction in 5 minutes | Log Reduction in 15 minutes |
|---|---|---|---|
| *ProPionibacterium acnes* ATCC6919 | 2.35 | 3.85 | 5.25 |
| *Propionibacterium acnes* Sauvage (ery R) | 2.15 | 3.6 | 5 |
| *Propionibacterium acnes* Sauvage (ery S) | 4.75 | >5.6 | >5.6 |

Even diluted at 20%, the composition retains good activity.

The invention claimed is:

1. A hygiene composition for the skin comprising zinc coceth sulfate as an antibacterial agent against *Propionibacterium acnes* combined with sodium lauroyl methyl isethionate, wherein
   zinc coceth sulfate represents from 5 to 20% by weight of the composition with respect to the total weight of the composition, and
   sodium lauroyl methyl isethionate represents from 5 to 20% by weight of the composition with respect to the total weight of the composition,
   with the proviso that said hygiene composition is devoid of salt or additional derivative of glycyrrhizic acid or glycyrrhetinic acid.

2. The hygiene composition for the skin according to claim 1, further containing an antibacterial agent chosen from among extract of myrtle, polyglyceryl-3 monocaprylate, glyceryl caprate, and cetrimonium bromide.

3. The hygiene composition for the skin according to claim 1, further containing an anti-seborrhoea agent chosen from among glyceryl laurate, a *sabal* extract, a pumpkin seed oil, and an extract of *urtica* dioic.

4. The hygiene composition for the skin according to claim 2, further containing an anti-seborrhoea agent chosen from among glyceryl laurate, a *sabal* extract, a pumpkin seed oil, and an extract of *urtica* dioic.

* * * * *